United States Patent [19]

Schellenberg et al.

[11] Patent Number: 4,676,979
[45] Date of Patent: Jun. 30, 1987

[54] METHOD OF PROTECTING ANIMALS AGAINST IONIZING RADIATION

[75] Inventors: Karl A. Schellenberg, Virginia Beach; James Shaeffer, Chesapeake, both of Va.

[73] Assignee: Eastern Virginia Medical Authority/Med. Ctr. Hosp., Norfolk, Va.

[21] Appl. No.: 791,012

[22] Filed: Oct. 24, 1985

Related U.S. Application Data

[63] Continuation-in-part of Ser. No. 686,632, Dec. 31, 1984, abandoned, which is a continuation of Ser. No. 527,060, Aug. 29, 1983, abandoned.

[51] Int. Cl.$^4$ .................... A61K 31/74; A61K 31/79
[52] U.S. Cl. ........................................ 424/80; 424/78; 514/723
[58] Field of Search ............................ 424/78, 79, 80; 514/723

[56] References Cited

U.S. PATENT DOCUMENTS

| 3,142,617 | 7/1964 | Lachman | 424/78 |
| 3,216,897 | 11/1965 | Krantz | 514/722 |
| 4,080,442 | 3/1978 | Mizutani | 514/53 |
| 4,423,033 | 12/1983 | Taskis | 424/80 |

Primary Examiner—Leonard Schenkman
Assistant Examiner—Joseph A. Lipovsky
Attorney, Agent, or Firm—Dale Lischer; J. Rodgers Lunsford, III

[57] ABSTRACT

There is disclosed a method of protecting animals including humans against ionizing radiation by injecting the animals with a polymer having the approximate formula $H(OCH_2CH_2)_nOH$, where n varies between 4 and 13. Particularly, it is found that polyethylene glycol (molecular weight between 200 and 600), polyethyleneglycolmonoethylether (molecular weight between 200 and 600), and polyvinylpyrrolidone (molecular weight up to 10,000) when injected into standard experimental animals, such as mice, protects them from the lethal effect of ionizing radiation.

4 Claims, No Drawings

METHOD OF PROTECTING ANIMALS AGAINST IONIZING RADIATION

RELATED APPLICATION

This is a continuation-in-part of Ser. No. 686,632, filed Dec.31, 1984 now abandoned which was a continuation of Ser. No. 527,060, filed Aug. 29, 1983, now abandoned.

BACKGROUND OF THE INVENTION

This invention concerns a method for protecting living organisms against ionizing radiation, and more particularly involves the administration of high molecular weight radiation protecting agents to living organisms to protect them against ionizing radiation.

In the early 1950s it was found that cysteamine and related aminoalkyl thiols could protect living organisms against ionizing radiation. In particular, when these substances were given to mice prior to exposure to x-rays, the substances reduced the lethal effect of the x-ray radiation. Since that time, searches have been underway to discover better radiation protecting agents. Prior to making the invention disclosed in the present application, the most promising agent was WR2721 (S-2(3-Aminopropylamino)-Ethyl-Phosphorothioic Acid), which breaks down in the body to an aminoalkyl thiol, and its effect is similar to that of cysteamine.

Radiation protecting agents are useful for treating people who are likely to be exposed to radiation including workers associated with atomic reactors, military personnel, and astronauts who may be exposed while in orbit to a sudden burst from a solar flare. Radiation protecting agents are also useful as adjuncts in the radiotherapy of cancer in which the radiation protecting agents will selectively protect normal tissue allowing the cancerous tissue to be destroyed by the radiation therapy. The radiation protecting agents, to date, however, have many shortcomings including high toxicity in humans and very limited degree of protection.

SUMMARY OF THE INVENTION

It is thus an object of the present invention to provide a method for protecting animals including humans against ionizing radiation by use of a class of high molecular weight radiation protecting agents.

It is also an object of the present invention to provide protection for animals including humans against ionizing radiation by the administration of radiation protecting agents comprising a polymer with the approximate formula $H(OCH_2CH_2)_nOH$, where n varies between 4 and 13.

It is a further object of the present invention to provide protection of animals including humans against ionizing radiation by the administration of radiation protecting agents including polyethylene glycol (molecular weight 400), polyvinylpyrrolidone (molecular weight 10,000), and polyethyleneglycolmonomethylether (molecular weight 400).

Other objects and advantages of the invention will become apparent upon reading the following detailed description.

DETAILED DESCRIPTION OF THE INVENTION

While the invention will be described in connection with a preferred embodiment and procedure, it will be understood that we do not intend to limit the invention to that embodiment or procedure. On the contrary, we intend to cover all alternatives, modifications, and equivalents as may be included within the spirit and scope of the invention as defined by the appended claims.

We have discovered that a prototype for radiation protecting agents, which are especially useful in protecting animals including humans against ionizing radiation, is embodied in a polymer with the approximate formula $H(OCH_2CH_2)_nOH$, where n varies between 4 and 13. One such substance is known commercially as polyethylene glycol 400 (molecular weight 400) and has been in existence for a number of years.

Polyethylene glycols are known to interreact with living cells causing a stabilization of the cell membrane, thereby promoting cell fusion and protection of cells against freezing. It is this phenomenon that is thought to account for the effectiveness of polyethylene glycol as a radiation protecting agent when administered prior to radiation.

The effectiveness of polyethylene glycol 400 as a radiation protecting agent is experimentally evidenced by the following protocol. Groups of 12 ICR male mice of about 25 to 28 grams each were injected intraperitoneally with 0.15 ml of polyethylene glycol 400 dissolved in 0.15 ml of water. The 1:1 solution was used to lower the viscosity of the polyethylene glycol 400 and thereby facilitate injection with a syringe. The polyethylene glycol can be injected undiluted in mice without harm, and it can be injected in more dilute form limited by the volume of solution that can be accommodated by the volume of the mouse's body. Ten minutes later the mice were anesthetized with pentobarbital, and twenty minutes later were irradiated with 1,650 rads of 250 kV x-rays limited to the head and neck. Control ICR male mice were irradiated in the same manner without being pretreated with polyethylene glycol 400.

Following irradiation, the mice were checked daily for fifteen days, and were examined for weight gain, symptoms, general appearance, and death from either administration of the drug or the radiation. The group which was injected with polyethylene glycol 400 experienced 2 out of 12 and 2 out of 12 deaths in two separate experiments. The control group with no injection of polyethylene glycol 400 experienced 9 out of 12 and 11 out of 12 deaths respectively.

The difference in survival is highly significant. Based on prior experiments in which death rates were correlated with radiation doses, the effect of the polyethylene glycol 400 treatment is the same as that of reducing the amount of radiation administered to untreated control groups of mice.

Polyethylene glycol 400 even provides protection when administered intraperitoneally after irradiation. In two experiments in which polyethylene glycol 400 in a 1:1 solution in water was injected five minutes after irradiation, only 6 out of 12 and 7 out of 12 mice were dead after fifteen days as compared to 10 out of 12 and 11 out of 12 untreated control mice.

Based on the experimental results of post radiation treatment, we have concluded that the mechanism of action involved in post-radiation treatment is something other than free radical scavenging which would only occur if the radiation protecting agent was present during radiation exposure. While the precise mechanism of post-radiation treatment with polyethylene glycol 400 is not known, the mechanism is probably related to polyethylene glycol's interaction with cellular membranes.

While polyethylene glycol having a molecular weight of 400 is preferred, we have found that significant radiation protection is achieved with polyethylene glycol having a molecular weight between 200 and 600. We have also determined that effective dosages of polyethylene glycol 400 for mice ranges from 1.6 grams per kilogram to 6.4 grams per kilogram. Because polyethylene glycol 400 is much less toxic than cystamine, WR2721, or other previously used radiation protecting agents, the maximum effective dose of 6.4 grams per kilogram is well below the $LD_{50}$ for poly- ethylene glycol 400 of approximately 9 grams per kilogram when injected intraperitoneally in mice.

Based on our experiments we have discovered no beneficial results in mice from treatment administered twenty-four hours before or three hours after irradiation. Therefore we have concluded that treatment should be undertaken within a short a period of time of the radiation as practical.

We have also discovered that polyethyleneglycolmonomethylether of various molecular weights and polyvinylpyrrolidone of various molecular weights also display radiation protection properties.

While polyethyleneglycolmonomethylether having molecular weights between 200 and 600 is an effective radiation protecting agent, we prefer polyethyleneglycolmonomethylether having a molecular weight of 400.

In experiments with polyethyleneglycolmonomethylether (molecular weight 400) conducted on mice in accordance with the protocol set out above, polyethyleneglycolmonomethyl- ether was given at a dosage of 6.4 grams per kilogram prior to the radiation of the mice. At that dosage level of polyethyleneglycolmonomethylether, only 3 out of 11 deaths occurred as compared to the usual experimental results with polyethylene glycol 400 in which between 0 and 2 out of 12 deaths occur in similar experiments.

With respect to polyvinylpyrrolidone having a molecular weight of 10,000, similar experiments conducted with a dose level of 11 grams per kilogram injected intraperitoneally prior to radiation. The results after 15 days yielded 3 out of 12 deaths again compared to between 0 and 2 out of 12 deaths for polyethylene glycol 400.

We claim:

1. A method of protecting animals including humans against ionizing radiation comprising injecting into the animals within a short time period from about thirty minutes prior to irradiation to about five minutes after irradiation, a dosage of between approximately 1.6 grams per kilogram and 6.4 grams per kilogram of body weight of a polymer having the approximate formula $H(OCH_2CH_2)_nOH$, wherein n varies between 4 and 13 and wherein said polymer is the sole active ingredient.

2. The method of claim 1 wherein the polymer is polyethylene glycol having a molecular weight between 200 and 600.

3. A method of protecting animals including humans against ionizing radiation comprising injecting into the animals within a short time period from about thirty minutes prior to irradiation to about five minutes after irradiation, a dosage of approximately 11 grams per kilogram of body weight of Polyvinylpyrrolidone having a molecular weight of up to 10,000 and wherein said polymer is the sole active ingredient.

4. A method of protecting animals including humans against ionizing radiation comprising injecting into the animals within a short time period from about thirty minutes prior to irradiation to about five minutes after irradiation, a dosage of approximately 6.4 grams per kilogram of body weight of Polyethyleneglycolmonomethylether having a molecular weight between 200 and 600 and wherein said polymer is the sole active ingredient.

* * * * *